United States Patent [19]
Bukrinsky et al.

[11] Patent Number: 6,019,979
[45] Date of Patent: Feb. 1, 2000

[54] ANTI-VIRAL TREATMENT WITH PERTUSSIS TOXIN B OLIGOMER

[75] Inventors: Michael Bukrinsky, Glenwood Landing; Massimo Alfano, Floral Park, both of N.Y.

[73] Assignee: The Picower Institute for Medical Research, Manhasset, N.Y.

[21] Appl. No.: 08/911,879

[22] Filed: Aug. 15, 1997

[51] Int. Cl.$^7$ .................................................. A01N 37/18
[52] U.S. Cl. .................... 424/204.1; 424/184.1; 424/201.1; 424/208.1; 424/254.1; 424/282.1; 514/2
[58] Field of Search .............................. 424/184.1, 201.1, 424/204, 208.1, 254.1, 282.1; 514/2

[56] References Cited

PUBLICATIONS

Locht and Keith *Science* 232:1258–1264, 1986.
Rosoff et al., *J. Immunol.* 139:2419–2423, 1987.
Rogers et al., *J. Immunol.* 145:678–683, 1990.
Ui, "Pertussis Toxin as a Valuable Probe for G–Protein Involvement in Signal Transduction".
Chong et al. *Infection Immunity* 60:4640–4647, 1992.
Wong and Rosoff, *Can. J. Physiol. Pharmacol.* 74:559–564, 1996.
Oka et al., "Enhancing Effects of Pertussis Toxin B Oligomer on the Immunogenicity of Influenza Vaccine Administered Intranasally", *Vaccine,* vol. 12, No. 14(1994), pp. 1255–1258.
Kenealy et al. "Antibodies from Human Immunodeficiency Virus–Infected Individuals Bind to a Short Amino Acid Sequence that Elicits Neutralizing Antibodies in Animals", *AIDS Research and Human Retroviruses,* vol. 5, No. 2(1989), pp. 173–182.
Chowdhury et al. "Pertussis Toxin Inhibits Induction of Human Immunodeficiency Virus Type 1 in Infected Monocytes" *Virology,* vol. 203, No. 2(Sep. 1994), pp. 378–383. QR1.V5.

*Primary Examiner*—Jeffrey Stucker
*Attorney, Agent, or Firm*—Davis Wright Tremaine LLP

[57] ABSTRACT

There is disclosed a method for anti-viral therapy treatment with the Pertussis toxin beta subunit oligomer, wherein the oligomer is composed of from two to ten subunits of PTX selected from the group consisting of S2, S3, S4, S5, and combinations thereof.

8 Claims, 11 Drawing Sheets

ANTI-VIRAL TREATMENT WITH PERTUSSIS TOXIN B OLIGOMER

TECHNICAL FIELD OF THE INVENTION

The present invention provides a method for anti-viral therapy treatment with the Pertussis toxin beta subunit.

BACKGROUND OF THE INVENTION

Viral infections are a continuing medical problem because, like any rapidly-dividing infectious agent, there are continuing mutations that help some sub-populations of viruses resistant to current treatment regimens. Many virally-based diseases do not have effective anti-viral treatments, because such treatments address the symptoms of the viral disease and not the root cause of the disease.

Pertussis toxin (PTX) is a 105,700 Dalton polypeptide that has both an alpha subunit and a beta subunit (PTBS). Pertussis toxin (PTX), a heterohexameric protein released by Bordetella Pertussis, exhibits diverse biological activities, mediated mostly by the A-subunit (A-promoter) which inactivates signaling pathways of members of the $G_i$–$G_0$ and $G_t$-protein family. Binding to the receptor and internalization of the toxin is mediated by the B-oligomer. The hexamer is composed of one S1 subunit having a molecular weight of 28 kDa, one S2 subunit having a molecular weight of 23 kDa, one S3 subunit having a molecular weight of 22 kDa, two S4 subunits having a molecular weight of 11.7 kDa, and one S5 subunit having a molecular weight of 9.3 kDa. The S1 examers constitute the active A promoter, and an oligomer composed of one each of the S2, S3, and S5 subunits plus two S4 subunits constitute the B-oligomer that is the binding region. (Ui, *Pertussis Toxin as a Probe of Receptor Coupling to Inositol Lipid Metabolism. Phosphoinositides and Receptor Mechanism*, pp 163–195. Alan R. Liss, Inc., 1986). In addition, the D1 oligomer is composed of one each of the S2 and S4 subunits and can bind to a p43 PTX receptor, and a D2-oligomer is composed of one each of the S3 and S4 subunits and can bind to a p70 PTX receptor (Wong and Rosoff "Pharmacology of Pertussis Toxin B" *Can. J. Physiol. Pharmacol.* 74:559–566, 1996).

The A-promoter is released from the holotoxin molecule as a result of an allosteric effect of intracellular ATP. Specifically, intracellular ATP binds to the S3 subunit of the B-oligomer. The active center of ADP-rybosil transferase, unmasked in the released A-promoter molecule, can interact with intracellular reduced glutathione, which cleavages disulfide bonds essential for enzymatic activity (Ui, *Pertussis Toxin as a Probe of Receptor Coupling to Inositol Lipid Metabolism. Phosphoinositides and Receptor Mechanism*, pp 163–195. Alan R. Liss, Inc., 1986). The A-subunit possesses adenine diphosphate (ADP) ribosyltransferase activity, which catalizes ADP-ribosylation of G-proteins, leading to their dissociation from receptors and uncoupling of corresponding signal transduction events. Due to this feature, PTX has become a very useful pharmacological tool for the identification of G proteins in the plasma membrane.

The B (binding) oligomer confers cell membrane-binding specificity by interacting with specific receptors. In lymphocytes, two PTX-binding proteins have been identified: a 43-kDa (Rogers et al., *J. Immunol.* 145:678–683, 1990) and a 70-kDa (Armstrong et al., *Infect. Immun.* 62:2236–2243, 1994) receptors. A leukocyte-specific integrin, Mac-1 (CD11b/CD18) may be a binding site for PTX on macrophages (Wong et al., *Immunology* 88:90–97, 1996). Occupation of these putative receptors by the B-oligomer can trigger phospholipase C (PLC) and tyrosine kinase-dependent signal transduction pathways. However, the effect of these events on the function of a target cell is not characterized, and pharmacological properties of the PTX B-oligomer are largely unknown. Nevertheless, the B-oligomer was shown to potentiate the immune response to intranasally administered influenza vaccine in mice when used as an adjuvant (Oka et al., *Vaccine* 12:1255–1258, 1994), and also induced resistance to lethal doses of mouse adenovirus infection (Winters et al., *Dev. Biol. Stand.* 61:233–240, 1985). The B-oligomer was shown to improve immune responses to viral vaccines, when used as an adjuvant (Oka et al., *Vaccine* 12:1255–1258, 1994; and Winters et al., *Dev. Biol. Stand.* 61:233–240, 1985).

In addition, whole Pertussis Toxin affected HIV replication in U1 cells (in vitro) wherein there was demonstrated a role of Gi protein PTX sensitivity in the U1 chronically infected monocytic cell line (Chowdury et al., *Virology* 203:378–383, 1994). In addition the stimulated PTX receptor can induce phospholipase C, which cuts off $PIP_2$ and produces $IP_3$ (inositol triphosphate) and DAG (diacyl glycerol) (Rosoff and Mohan, *J. Immunol.* 149:3191–3199, 1992). The PTX receptor further appears to require the coexpression of a CD3/TCR complex (Gray et al., $J_,$. *Immunol.* 142:1631–1638, 1989). Moreover, concentrations of the beta subunit of PTX (100 nM) stimulated production of interleukin-2 (IL-2) with a similar pattern seen with the antibody OKT3 in vitro in Jurkat cells (Rosoff et al., *J. Immunol.* 139:2419–2423, 1987).

Anti-viral therapies directed against the virus (as opposed to directed to symptoms of the disease) have generally been based upon viral enzymatic inhibition, such as HIV therapies directed against viral reverse transcriptase or viral protease enzymes. Therefore, there is a need in the art to discover and develop new anti-viral therapies that are not based upon a mechanism of action to inhibit virus-specific enzyme that is used in viral replication.

SUMMARY OF THE INVENTION

The present invention provides a method for treating viral infections, comprising administering an effective amount of Pertussis toxin β subunit oligomer (PTBS) to a patient having a viral infection. Preferably, the daily dose administered is from about 0.1 mg to about 500 mg. Preferably, the viral infection is caused by HIV. The PTBS oligomer is composed of combinations of from two to ten subunits of PTX selected from the group consisting of S2, S3, S4, S5, and combinations thereof. Preferably, PTBS is selected from the group consisting of 1S2-1S4, 1S3-1S4, 1S2-1S3-2S4-1S5, 1S2-1S3-2S4, and 1S2-1S4-1S3-1S4-1S5.

The present invention further provides an anti-HIV vaccine, comprising a HIV antigen or antigens and PTBS oligomer as a HIV vaccine adjuvant, wherein the PTBS oligomer is composed of from two to ten subunits of PTX selected from the group consisting of S2, S3, S4, S5, and combinations thereof. Preferably, PTBS is selected from the group consisting of 1S2-1S4, 1S3-1S4, 1S2-1S3-2S4-1S5, 1S2-1S3-2S4, and 1S2-1S4-1S3-1S4-1S5. In addition, the present invention provides a method of treating HIV infection, comprising administering an effective amount of an anti-HIV vaccine, wherein the anti-HIV vaccine comprises a HIV antigen or antigens and PTBS oligomer as a HIV vaccine adjuvant, wherein the PTBS oligomer is composed of from two to ten subunits of PTX selected from the group consisting of S2, S3, s4, S5, and combinations thereof. Preferably, PTBS is selected from the group consisting of 1S2–1S4, 1S3-1S4, 1S2-1S3-2S4-1S5, 1S2-1S3-2S4, and 1S2-1S4-1S3-1S4-1S5.

BRIEF DESCRIPTION OF THE DRAWINGS

FIG. 1 shows the results when primary T cells were infected with NSI strain of HIV (92U660 a macrophage-tropic primary HIV-1 isolate) and either 1 nM or 0.1 nM of PTBS oligomer (specifically, 1S1-1S2-1S3-2S4-1S5) was added to the cultures. Cell proliferation was measured by tritiated thymidine uptake (left panel) and anti-viral activity was measured by RT (reverse transcriptase) activity in culture supernatants collected every 3 days (right panel). FIG. 2 shows the results when primary T cells were infected with SI strain of HIV-$1_{LAI}$ (a T cell tropic HIV-1 strain) and either 1 nM or 0.1 nM of PTBS oligomer (specifically, 1S2-1S3-2S4-1S5) was added to the cultures. Cell proliferation was measured by tritiated thymidine uptake (left panel) and anti-viral activity was measured by RT (reverse transcriptase) activity in culture supernatants collected every 3 days (right panel). These data show anti-viral activity of PTBS oligomer in a dose response fashion in this predictive assay.

FIG. 3 shows a comparison of RT inhibition in culture supernatants measured as a ratio of RT activity in cells (92US660 in the left panel and HIV-$1_{LAI}$ in the right panel) pre-treated with different concentrations of PTBS oligomer (specifically, 1S2-1S3-2S4-1S5) and untreated cells. RT activity was tested at the peak of viral infection on day 9 and MIP-1α was tested in the same culture supernatants by ELISA.

FIG. 5 shows the effect of 18 hours of pre-treatment with PTBS oligomer (specifically, 1S2-1S3-2S4-1S5) (0.1 nM) all time after infection or one time (1 t) on RANTES production (measured by ELISA) in primary T cells infected by T cell line tropic (LAI) HIV-1 strains.

DETAILED DESCRIPTION OF THE INVENTION

Anti-Viral Method of Treatment

Figure 1:
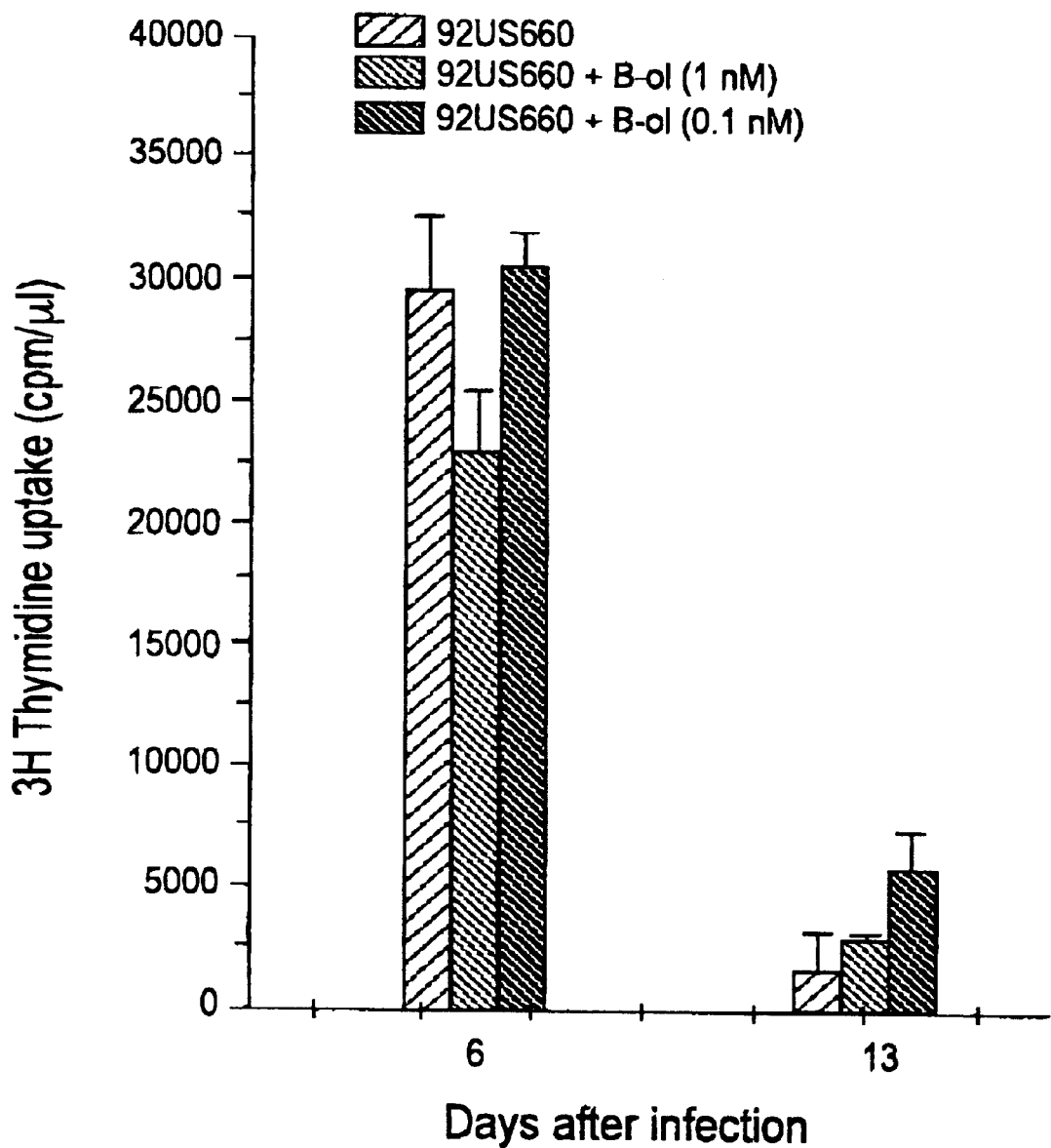
FIGS. 1 and 2 provide the results of a study showing the inhibitory effects of PTBS oligomer on HIV-1 replication in primary T cells. Specifically.
Figure 1:
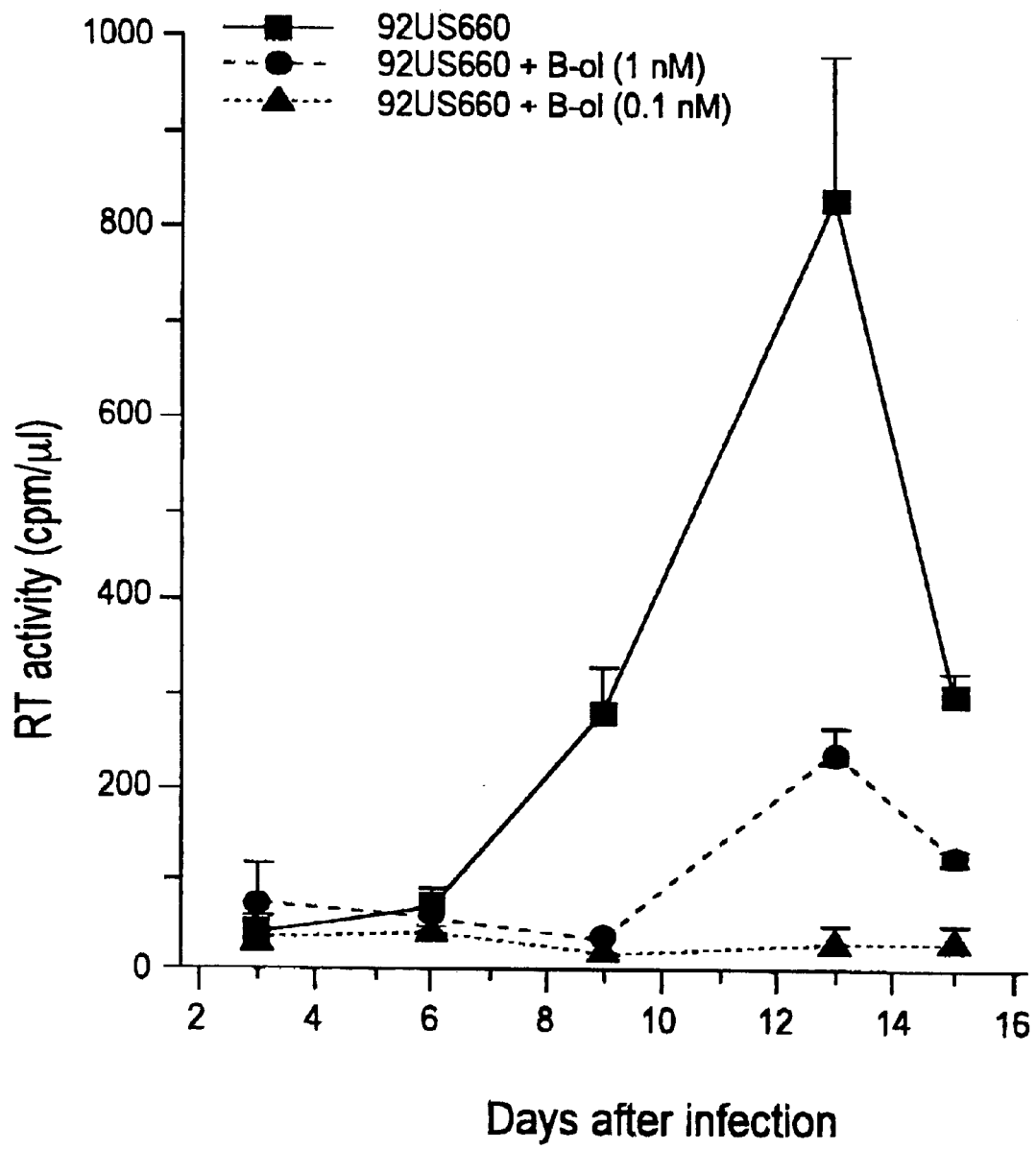

The present invention provides a method for treating viral infections, comprising administering an effective amount of Pertussis toxin β subunit oligomer (PTBS) to a patient having a viral infection, wherein the PTBS oligomer is composed of from two to ten subunits of PTX selected from the group consisting of S2, S3, S4, S5, and combinations thereof. Preferably, the daily dose administered is from about 0.01 mg to about 500 mg. Preferably, the viral infection is caused by HIV. The data provided herein in predictive assays of anti-viral activity support the claimed method of use.

PTBS

PTBS oligomer (specifically, 1S2-1S3-2S4-1S5 oligomer) is available commercially (e.g., Sigma or Calbiochem) in laboratory reagent quantities. PTBS oligomer, according to the present invention, is composed of from two to ten subunits wherein the subunits are S2, S3, S4, and S5. The sequence characterization and molecular weights of each subunit is known in the art (see, for example, Tamura et al., *Biochemistry* 21:5516–5522, 1982; and Nicosia et al., *Proc. Nati. Acad. Sci. USA* 83:4631–4635, 1986). The designation "2S2-1S3" for example refers to an oligomer composed of two S2 subunits and one S3 subunit. Similarly, the preferred 1S1-1S2-1S3-2S4-1S5 oligomer is a six subunit oligomer having one S1, one S2, one S3, two S4s and one S5 subunits.

Pharmaceutical Formulation

The inventive method in the form of a pharmaceutical composition comprising PTBS oligomer can be administered to a patient either by itself (complex or combination) or in pharmaceutical compositions where it is mixed with suitable carriers and excipients. PTBS oligomer can be administered parenterally, such as by intravenous injection or infusion, intraperitoneal injection, subcutaneous injection, or intramuscular injection. PTBS oligomer can be administered orally or rectally through appropriate formulation with carriers and excipients to form tablets, pills, capsules, liquids, gels, syrups, slurries, suspensions and the like. PTBS oligomer can be administered topically, such as by skin patch, to achieve consistent systemic levels of active agent. PTBS oligomer is formulated into topical creams, skin or mucosal patch, liquids or gels suitable to topical application to skin or mucosal membrane surfaces. PTBS oligomer can be administered by inhaler to the respiratory tract for local or systemic treatment of HIV infection.

The dosage of PTBS oligomer suitable for use with the present invention can be determined by those skilled in the art from this disclosure. PTBS oligomer will contain an effective dosage (depending upon the route of administration and pharmacokinetics of the active agent) of PTBS and suitable pharmaceutical carriers and excipients, which are suitable for the particular route of administration of the formulation (i.e., oral, parenteral, topical or by inhalation). The active PTBS oligomer is mixed into the pharmaceutical formulation by means of mixing, dissolving, granulating, dragee-making, emulsifying, encapsulating, entrapping or lyophilizing processes. The pharmaceutical formulations for parenteral administration include aqueous solutions of the active PTBS oligomer in water-soluble form. Additionally, suspensions of the active PTBS oligomer may be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. The suspension may optionally contain stabilizers or agents to increase the solubility of the complex or combination to allow for more concentrated solutions.

Pharmaceutical formulations for oral administration can be obtained by combining the active compound with solid excipients, such as sugars (e.g., lactose, sucrose, mannitol or sorbitol), cellulose preparations (e.g., starch, methyl cellulose, hydroxypropylmethyl cellulose, and sodium carboxymethyl cellulose), gelaten, gums, or polyvinylpyrrolidone. In addition, a desintegrating agent may be added, and a stabilizer may be added.

Use of PTBS as a Vaccine Adjuvant

No effective vaccination can be achieved without the use of a potent adjuvant. The mechanisms by which some adjuvants, such as alumn or Freud's adjuvant, potentiate immune response to an immunogen is up-regulation of cytokine production by certain target cells (TH1 lymphocytes for alumn and TH2 cells for Freud's adjuvant). PTBS oligomer can be used as an adjuvant for HIV vaccine. The data provided herein show that HIV-1 down-regulates β-chemokine production in infected T lymphocytes, thus reducing the protective effect of this potent anti-HIV mechanism, while PTBS can negate this HIV action. Therefore, PTBS oligomer stimulates uninfected T cells and restores the compromised capacity of infected T lymphocytes to produce β-chemokines.

Accordingly, the present invention provides an anti-HIV vaccine, comprising a HIV antigen or antigens and PTBS oligomer as a HIV vaccine adjuvant, wherein the PTBS oligomer is composed of from two to ten subunits of PTX selected from the group consisting of S2, S3, s4, S5, and combinations thereof. Preferably, PTBS is selected from the group consisting of 1S2-1S4, 1S3-1S4, 1S2-1S3-2S4-1S5, 1S2-1S3-2S4, and 1S2-1S4-1S3-1S4-1S5. In addition, the present invention provides a method of treating HIV infection, comprising administering an effective amount of an anti-HIV vaccine, wherein the anti-HIV vaccine comprises a HIV antigen or antigens and PTBS oligomer as a HIV vaccine adjuvant, wherein the PTBS oligomer is composed of from two to ten subunits of PTX selected from the group consisting of S2, S3, S4, S5, and combinations thereof. Preferably, PTBS is selected from the group consisting of 1S2-1S4, 1S3-1S4, 1S2-1S3-2S4-1S5, 1S2-1S3-2S4, and 1S2-1S4-1S3-1S4-1S5.

EXAMPLE 1

Figure 2:
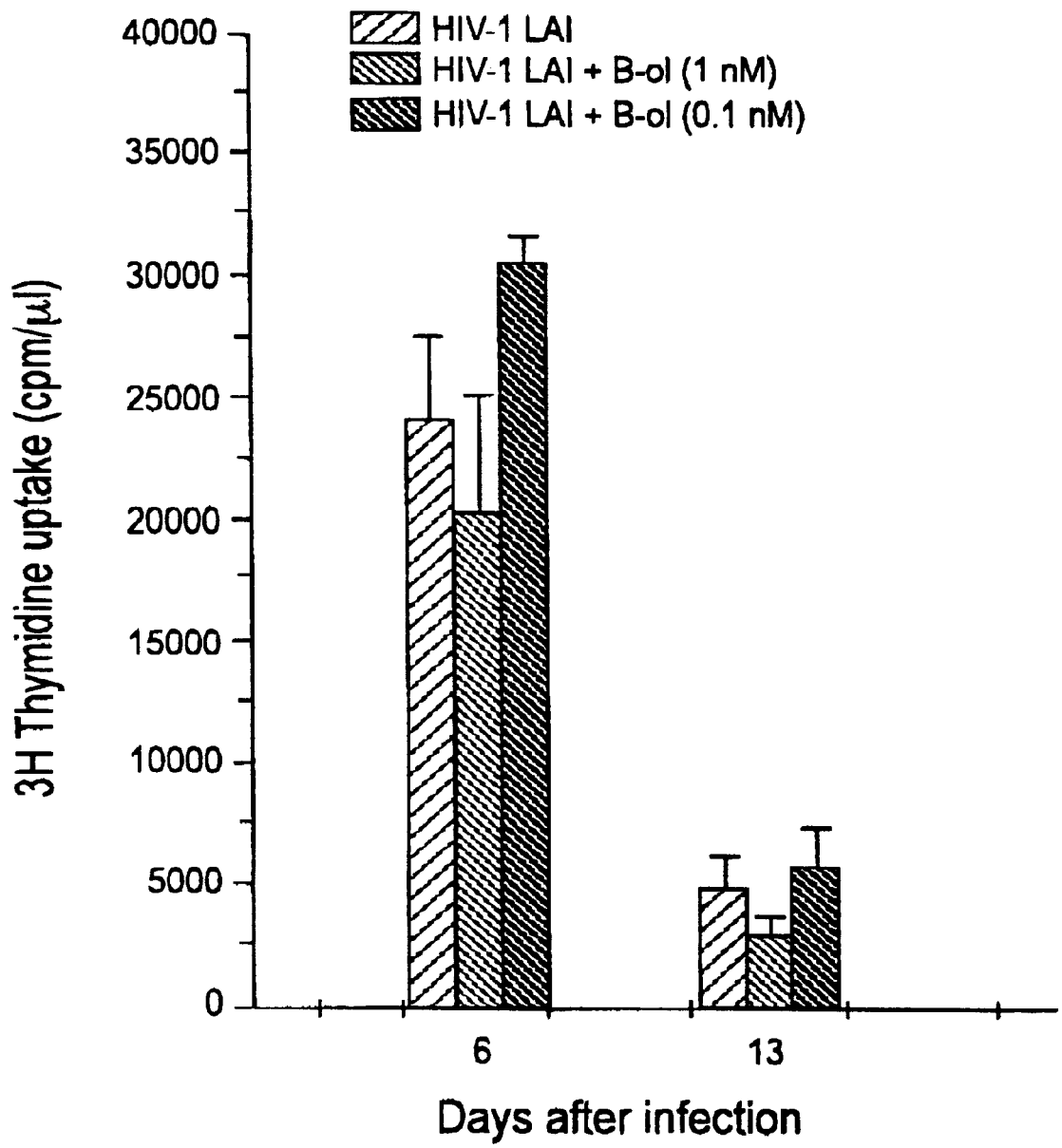
Figure 2:
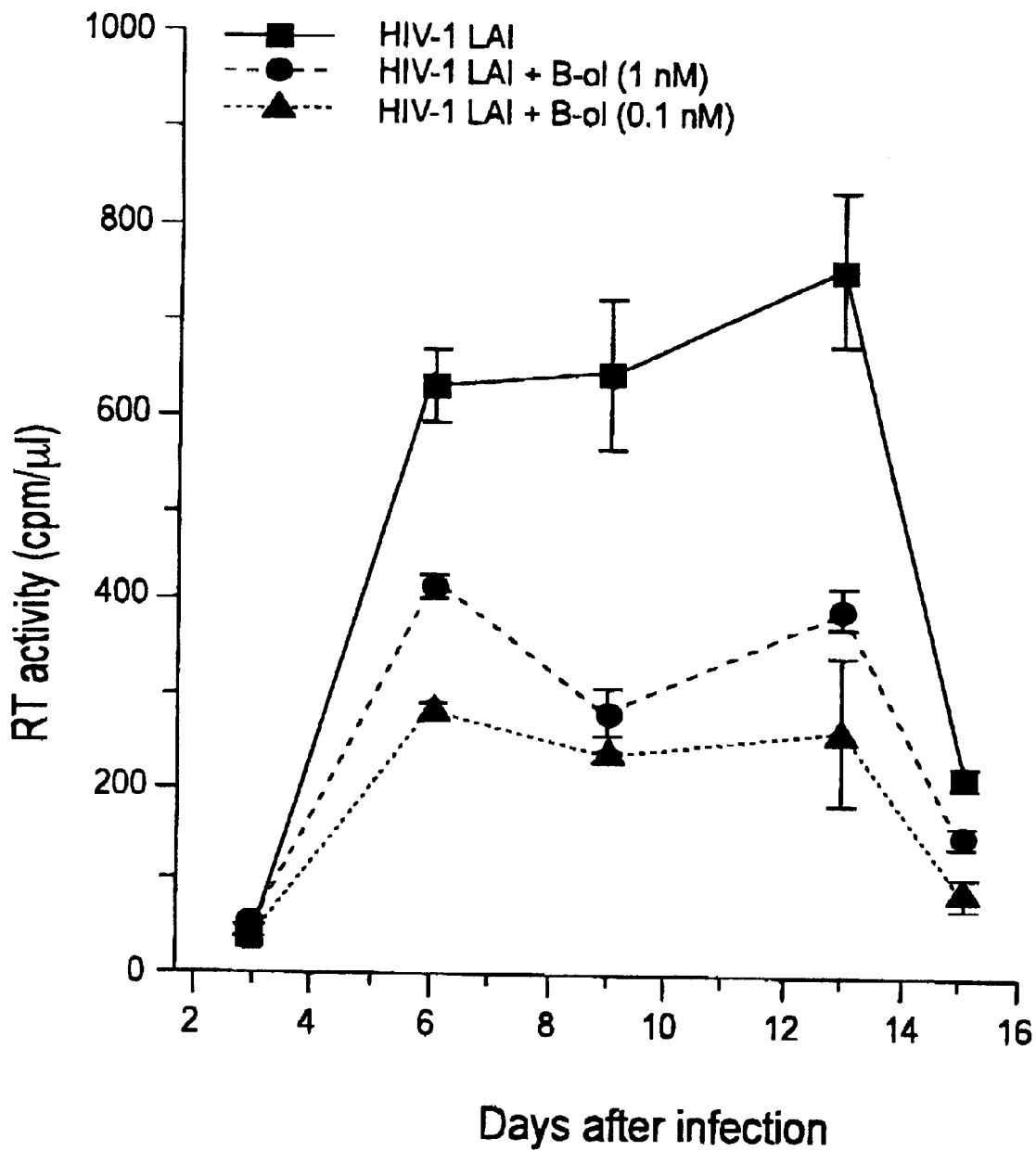

This example illustrates an experiment showing the inhibitory effects of PTBS on HIV-1 replication in primary T cells. Treatment of primary T cells with PTBS resulted in a complete inhibition of replication of both macrophage-tropic and T cell tropic HIV-1 strains, without affecting T cell proliferation and viability. Specifically, FIG. 1 shows the results when primary T cells were infected with NSI strain of HIV (92U660 a macrophage-tropic primary HIV-1 isolate) and either 1 nM or 0.1 nM of PTBS was added to the cultures. Cell proliferation was measured by tritiated thymidine uptake (left panel) and anti-viral activity was measured by RT (reverse transcriptase) activity in culture supernatants collected every 3 days (right panel). FIG. 2 shows the results when primary T cells were infected with SI strain of HIV-1$_{LAI}$ (a T cell tropic HIV-1 strain) and either 1 nM or 0.1 nM of PTBS was added to the cultures. Cell proliferation was measured by tritiated thymidine uptake (left panel) and anti-viral activity was measured by RT (reverse transcriptase) activity in culture supernatants collected every 3 days (right panel). These data show anti-viral activity of PTBS in a dose response fashion in this predictive assay.

EXAMPLE 2

Figure 3:
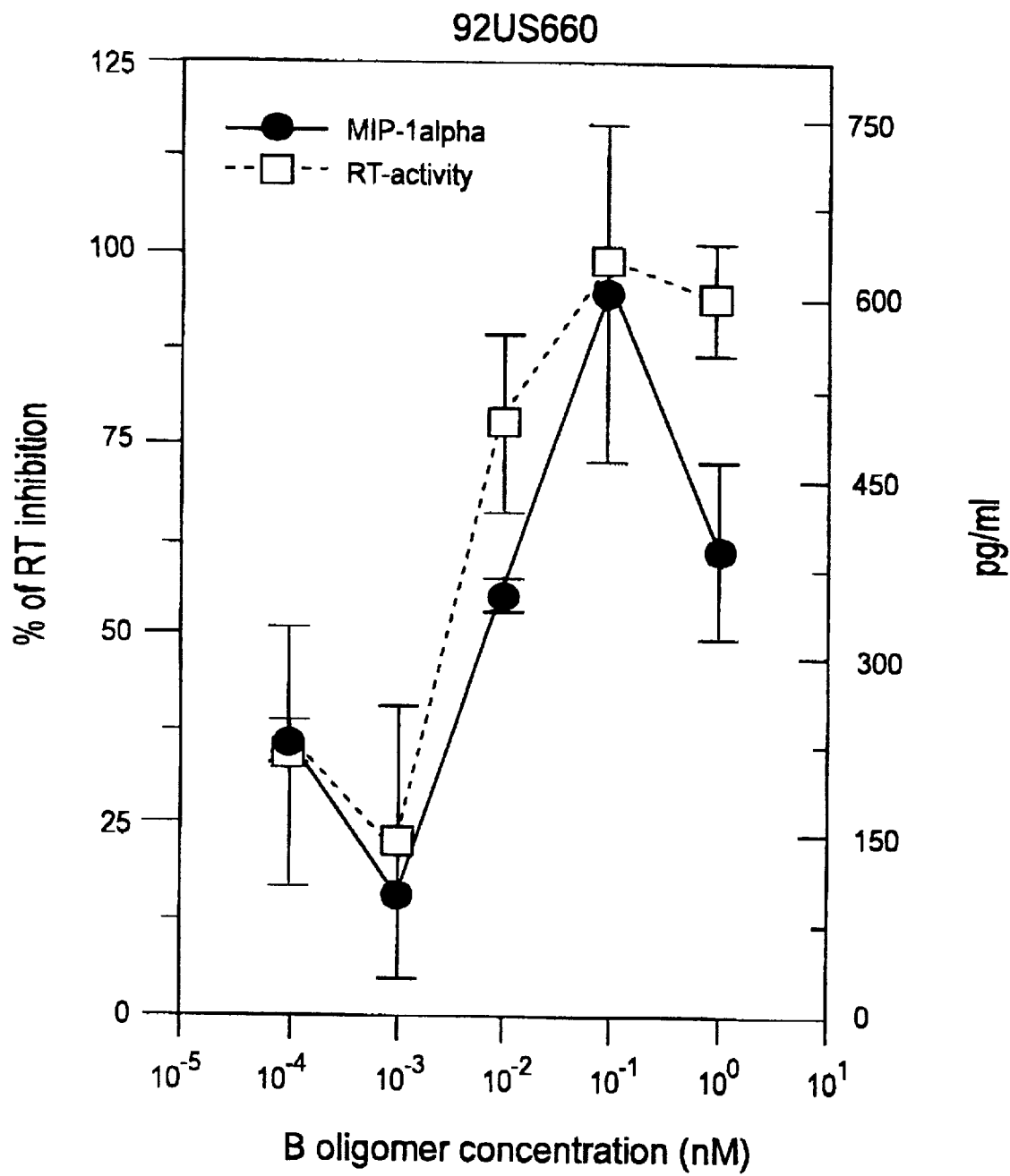
FIG. 3 shows that pretreatment of T lymphocytes with PTBS oligomer induces production of β-chemokines (MIP-1α, MIP-1β and RANTES) and their levels correlated with suppression of viral replication. Specifically.
Figure 3:
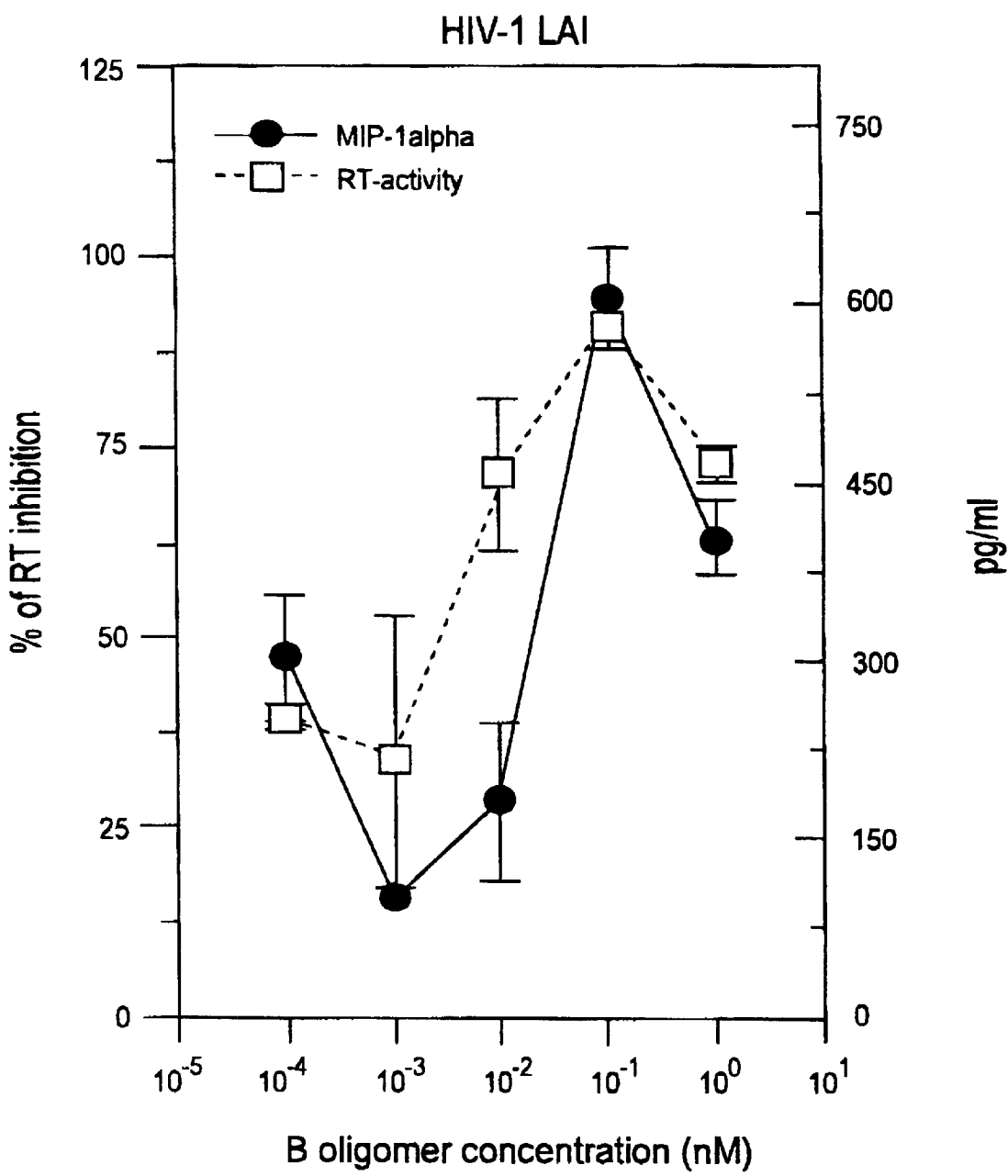

This example illustrates results of experiments wherein primary T cell cultures treated with PTBS displayed increased levels of β-chemokines (MIP-1α, MIP-1β and RANTES), which are potent suppressors of macrophage-tropic strains of HIV-1 in primary T cells. Specifically, FIG. 3 shows that pretreatment of T lymphocytes with PTBS induces production of β-chemokines (MIP-1, MIP-1β and RANTES) and their levels correlated with suppression of viral replication. FIG. 3 shows a comparison of RT inhibition in culture supernatants measured as a ratio of RT activity in cells (92US660 in the left panel and HIV-1$_{LAI}$ in the right panel) pre-treated with different concentrations of PTBS and untreated cells. RT activity was tested at the peak on day 9 and MIP-1α was tested in the same culture supernatants by ELISA.

EXAMPLE 3

Figure 4:
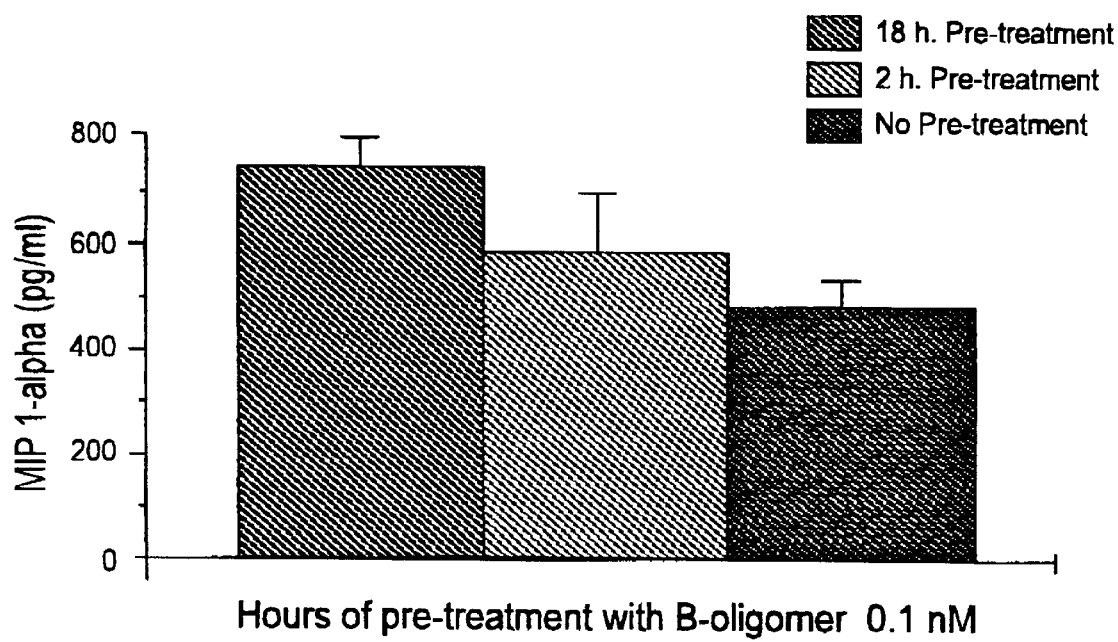
FIG. 4 (top panel) shows a comparison of hours of pretreatment with PTBS oligomer (specifically, 1S2-1S3-2S4-1S5) (0.1 nM) demonstrating that 2 hours pretreatment is enough to increase levels of β-chemokines in normal primary T cells. Similarly, the bottom panel shows that PTBS oligomer (specifically, 1S2-1S3-2S4-1S5) can influence an already-established HIV-1 infection, since adding 3 days after infection can still decrease RT activity.
Figure 4:
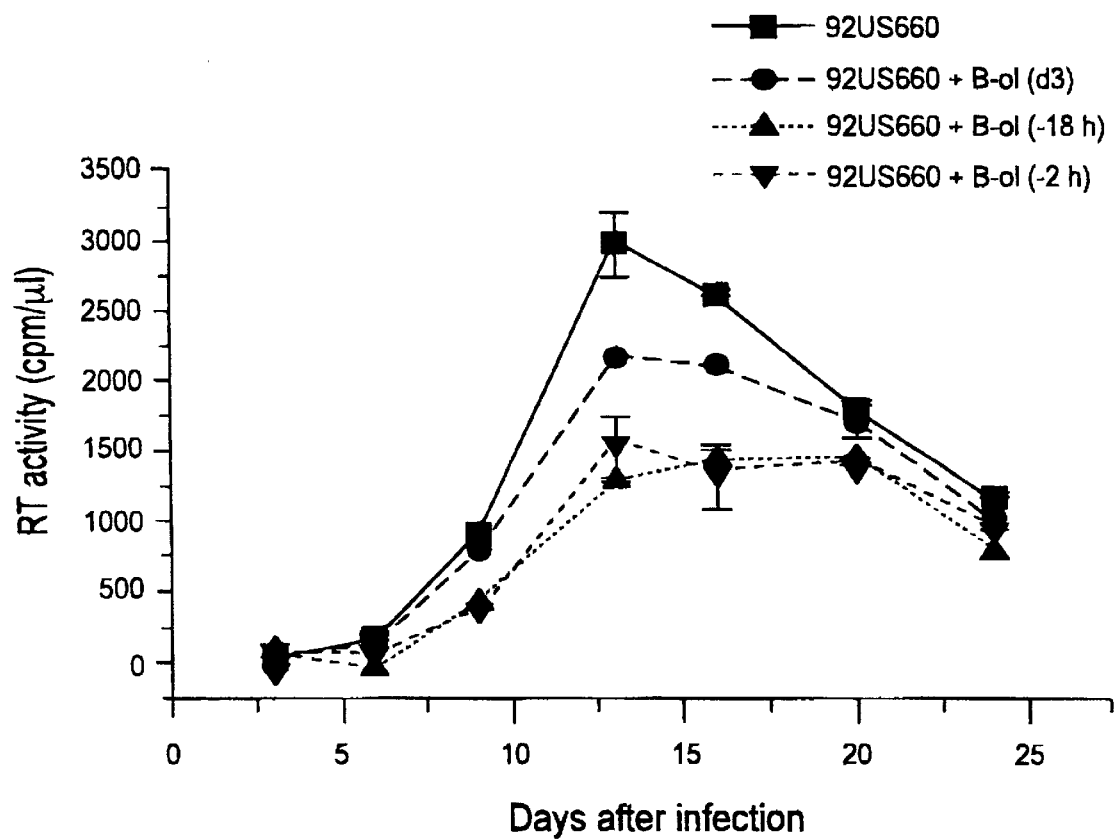

This example illustrates the PTBS dosing schedules, as coordinated with infection times, needed to cause an increase in the levels of β-chemokines in normal primary T cells. FIG. 4 (top panel) shows a comparison of hours of pretreatment with PTBS (0.1 nM) demonstrating that 2 hours pretreatment is enough to increase levels of β-chemokines in normal primary T cells. Similarly, the bottom panel shows that PTBS can influence an already-established HIV-1 infection, since adding 3 days after infection can still decrease RT activity. FIG. 4 shows the effect of 18 hour (−18 h) and 2 hours (−2) of pre-treatment with PTBS (0.1 nM) on MIP-1α and RT activity. Three day post infection treatment (d3) by PTBS could still inhibit HIV replication.

EXAMPLE 4

Figure 5:
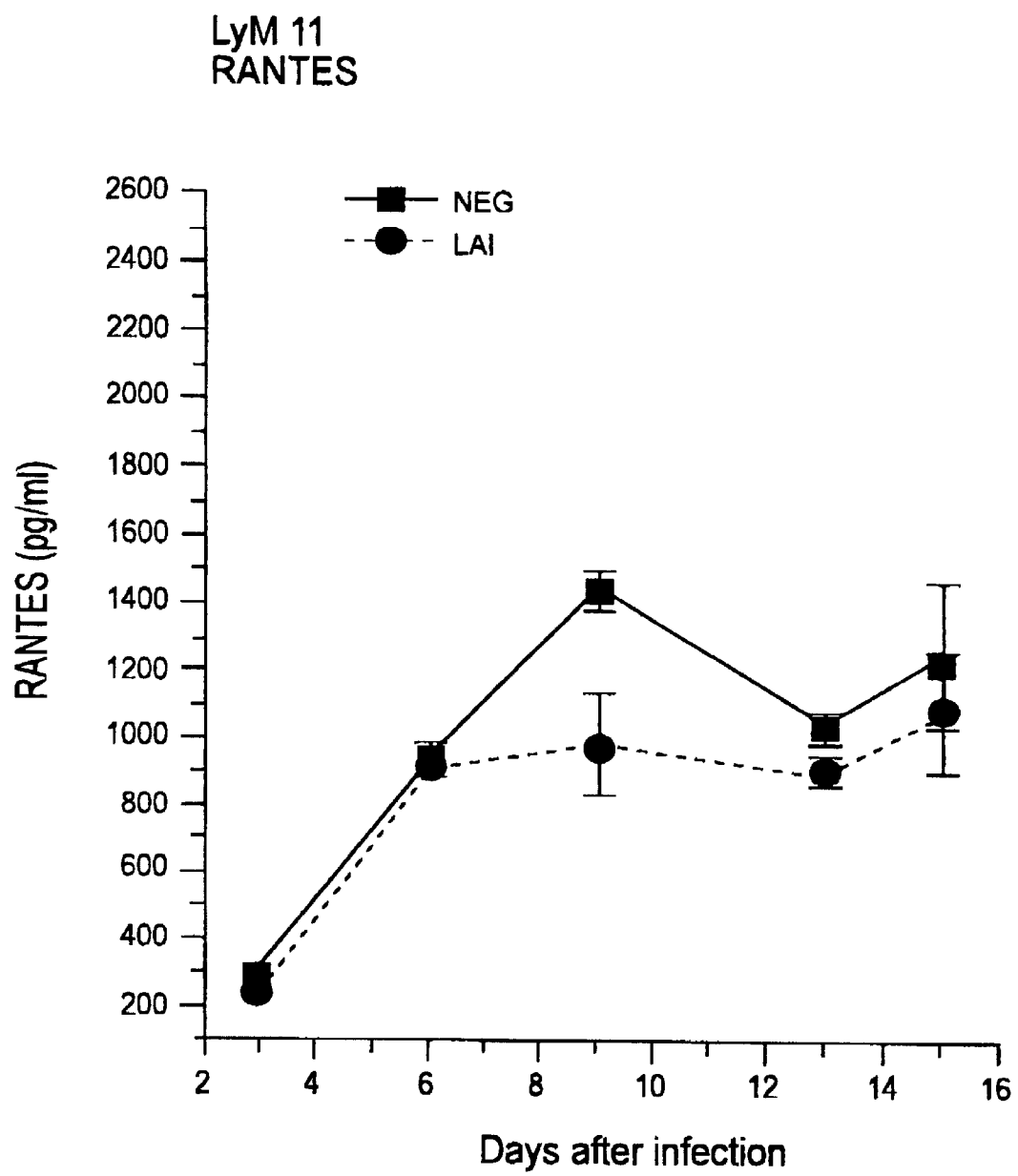
FIG. 5 shows that PTBS oligomer is able to induce up-regulation of β-chemokines when added once immediately after infection, without any difference versus the condition with all time treatment. Specifically.
Figure 5:
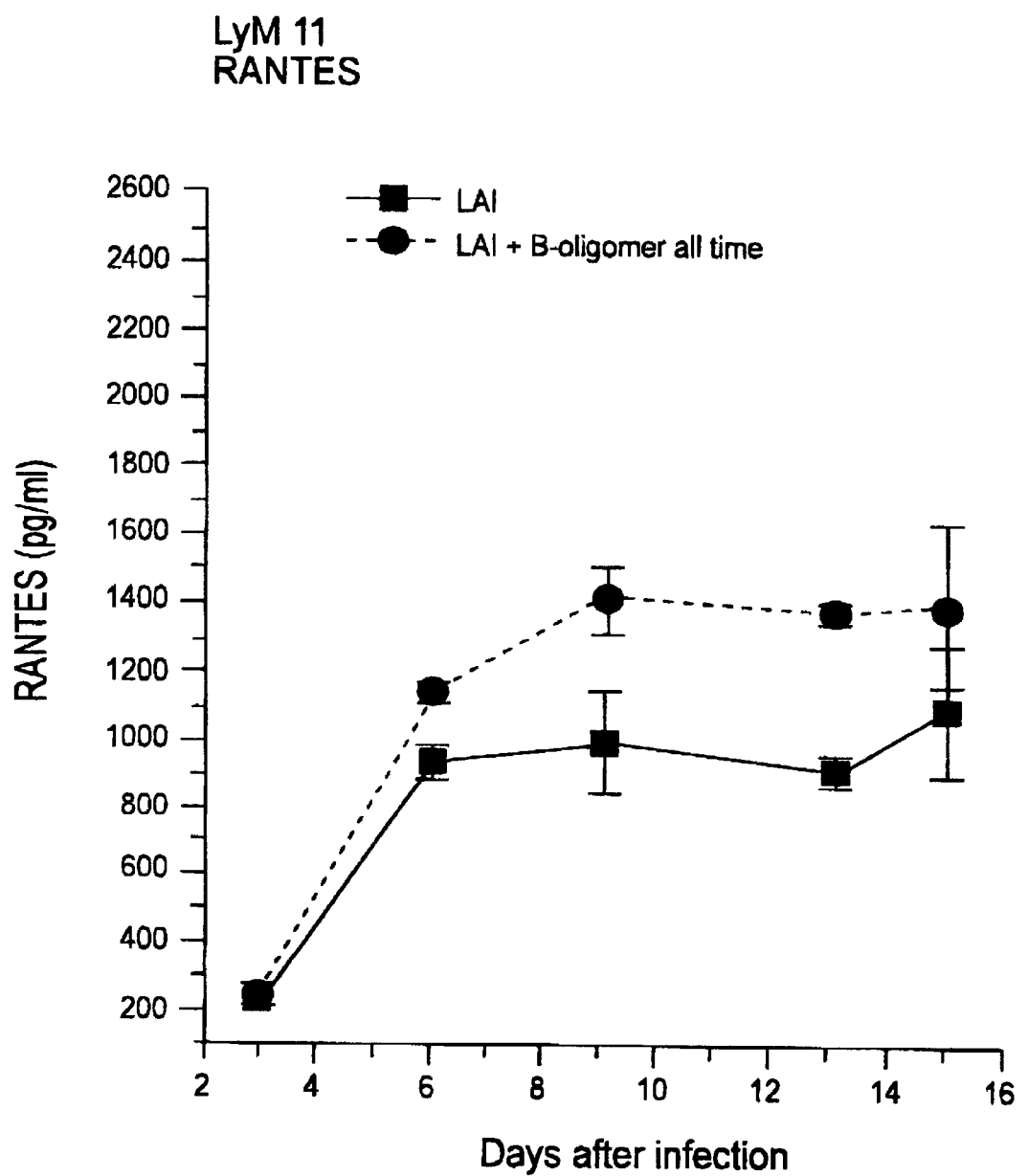
Figure 5:
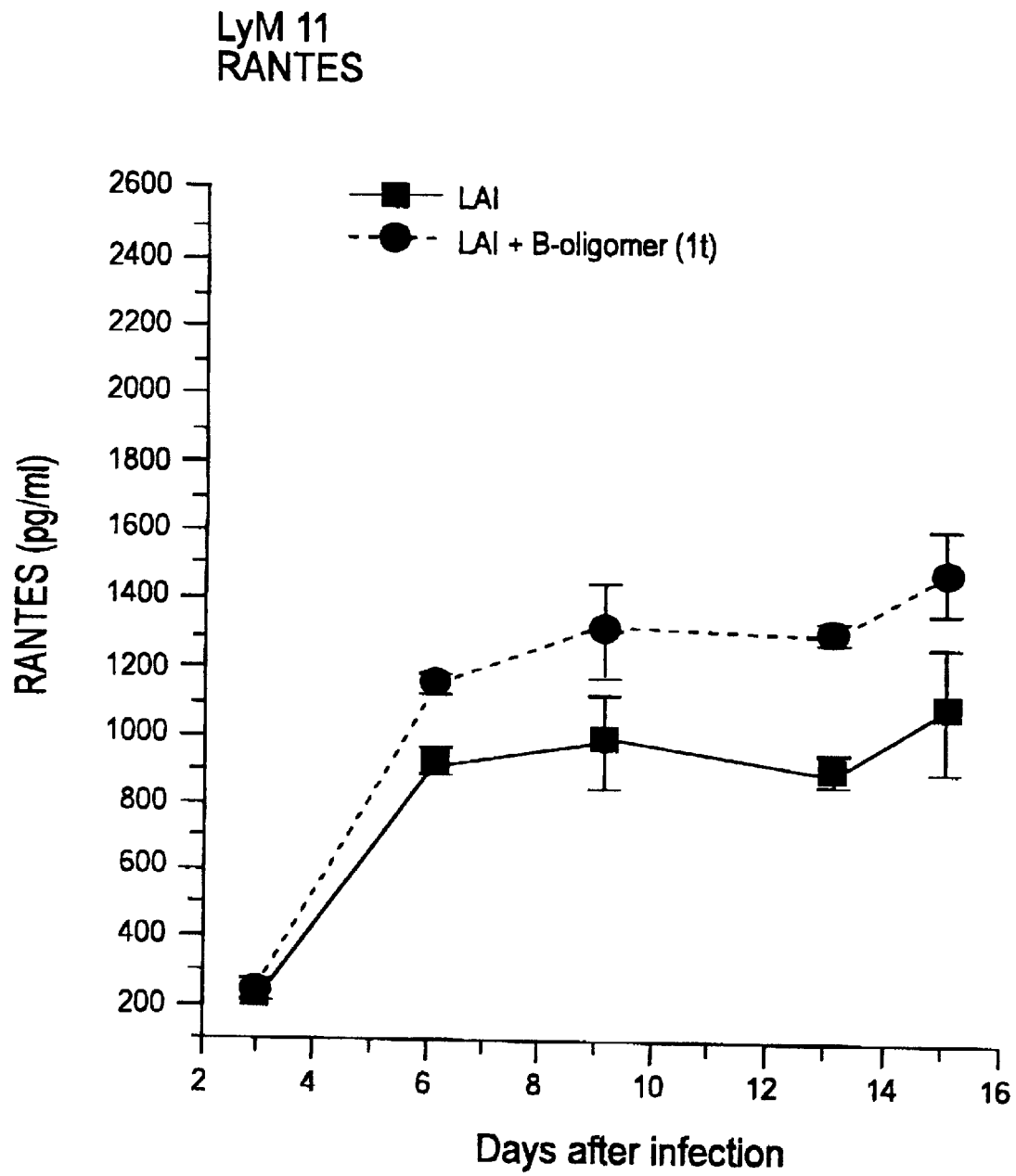

This example illustrates that PTBS was able to induce up-regulation of β-chemokines when added once immediately after infection, without any difference versus the condition with all time treatment. Specifically, FIG. 5 shows the effect of 18 hours of pre-treatment with PTBS (0.1 nM) all time after infection or one time (1 t) on RANTES production (measured by ELISA). Both macrophage tropic (92US660) and T cell line tropic (LAI) HIV-1 strains were inhibited.

β-chemokines can inhibit infection of T lymphocytes with macrophage-tropic, but not with T-cell-line-tropic viruses (Cocchi et al.. Science 270:1811–15, 1995). T lymphocytes do not produce SDF-1 (a ligand for the CXCR4 receptor used by T-cell-tropic strains). Therefore, these data suggest that mechanisms other than β-chemokines induction are involved in anti-HIV activity of PTBS.

We claim:

1. A method for treating viral infections, comprising administering an effective amount of B. pertussis toxin β(PTB) oligomer to a patient having a viral infection, wherein the PTB oligomer is composed of from two to ten subunits of PTX selected from the group consisting of S2, S3, S4, S5, and combinations thereof.

2. The method of claim 1 wherein the dose of PTB administered each day is from about 0.01 mg to about 500 mg.

3. The method of claim 1 wherein the viral infection is caused by HIV.

4. The method of claim 1 wherein the PTB oligomer is selected from the group consisting of 1S2-1S4, 1S3-1S4, 1S2-1S3-2S4-1S5, 1S2-1S3-2S4, and 1S2-1S4-1S3-1S4-1S5.

5. An anti-HIV vaccine, comprising at least one HIV antigen or antigens and PTB oligomer, wherein the PTB oligomer is composed of from two to ten subunits of PTX selected from the group consisting of S2, S3, S4, S5, and combinations thereof.

6. The anti-HIV vaccine of claim 5 wherein the PTB oligomer is selected from the group consisting of 1S2-1S4, 1S3-1S4, 1S2-1S3-2S4-1S5, 1S2-1S3-2S4, and 1S2-1S4-1S3-1S4-1S5.

7. A method for treating HIV infection for a patient having an HIV infection, comprising administering an effective amount of an anti-HIV vaccine, wherein the anti-HIV vaccine comprises a HIV antigen or antigens and PTB oligomer, wherein the PTB oligomer is composed of from two to ten subunits of PTX selected from the group consisting of S2, S3, S4, S5, and combinations thereof.

8. The method of claim 7 wherein the PTB oligomer is selected from the group consisting of 1S2-1S4, 1S3-1S4, 1S2-1S3-2S4-1S5, 1S2-1S3-2S4, and 1S2-1S4-1S3-1S4-1S5.

* * * * *